(12) United States Patent
Butt et al.

(10) Patent No.: US 7,501,500 B2
(45) Date of Patent: Mar. 10, 2009

(54) INHIBITING DENATURATION OF NUCLEIC ACID DUPLEXES

(75) Inventors: Neil Butt, Cambridge (GB); Matthew Baker, Cambridge (GB); Navin Deepal Pathirana, Cape Elizabeth, ME (US)

(73) Assignee: Whatman, Inc., Florham Park, NJ (US)

( * ) Notice: Subject to any disclaimer, the term of this patent is extended or adjusted under 35 U.S.C. 154(b) by 0 days.

(21) Appl. No.: 11/810,593

(22) Filed: Jun. 5, 2007

(65) Prior Publication Data

US 2007/0281316 A1 Dec. 6, 2007

Related U.S. Application Data

(62) Division of application No. 10/276,886, filed as application No. PCT/GB01/02564 on Jun. 11, 2001, now Pat. No. 7,244,561.

(30) Foreign Application Priority Data

Jun. 12, 2000 (GB) ................................. 0014324.8

(51) Int. Cl.
*C07H 19/00* (2006.01)
*C07H 21/04* (2006.01)
*C07K 14/00* (2006.01)

(52) U.S. Cl. ...................... 536/22.1; 536/23.1; 530/350

(58) Field of Classification Search ................ 536/22.1, 536/23.1; 435/6; 530/350
See application file for complete search history.

(56) References Cited

U.S. PATENT DOCUMENTS

| | | | |
|---|---|---|---|
| 4,668,618 A * | 5/1987 | Thornthwaite | 435/6 |
| 5,328,825 A * | 7/1994 | Warren et al. | 435/6 |
| 5,756,126 A | 5/1998 | Burgoyne | |
| 5,922,536 A | 7/1999 | Nivens et al. | |
| 6,670,128 B2 | 12/2003 | Smith et al. | |
| 6,844,158 B1 | 1/2005 | Mitsuhashi | |

FOREIGN PATENT DOCUMENTS

| | | |
|---|---|---|
| EP | 814156 A2 | 12/1997 |
| WO | WO 95/04140 | 2/1995 |
| WO | WO 00/21973 | 4/2000 |

OTHER PUBLICATIONS

Marguet et al. Protection of DNA by salts against thermodegradation at temperatures typical for hyperthermophiles. Extremophiles, vol. 2, pp. 115-122, 1998.*

Akamatsu et al. "A simple and rapid extraction of high molecular weight chromosomal DNA from *bacillus subilis* protoplasts for cosmid cloning and interspecific transformation," *Biosci.Biotechnol. Biochem.*, 2000, pp. 1082-1083, vol. 64(5).

Cooper, Geoffrey M., "The Cell: A Molecular Approach," 1997, Sinauer Associates, pp. 42-54; pp. 316-320.

Cullinane, C. and Phillips, D.R., "Thermal Stability of DNA adducts induced by Cyanomorpholinoadriamycin in vitro," *Nucleic Acids Research*, 1993, pp. 1857-1862, 21:(8).

Grayling, R.A., et al., "DNA Stability and DNA Binding Proteins," *Advances in Protein Chemistry*, 1996, pp. 437-467, vol. 48.

Grayling, R.A., et al., "Histones and chromatin structure in hyperthermophilic *Archaea*," *FEMS Microbiology Reviews*, 1996, pp. 203-213, vol. 18.

Guagliardi A., et al., "Annealing of complementary DNA strands above the melting point of the duplex promoted by an archaeal protein". *J Mol Biol.*, Apr. 11, 1997, pp. 841-848, vol. 267(4).

Hamaguchi, K. and Geiduschek, E.P., "The Effect of Electrolytes on the Stability of the Deoxyribonucleate Helix," *JACS*, 1962, pp. 1329-1338, vol. 84:(8).

Johnson, J.D., et al., "DNA-Binding Proteins from Novikoff Hepatoma Cells," *Biochem. Biophys Acta.* 1975, pp. 424-438, vol. 37. *J. Dairy Sci.* 55: 1972, pp. 696-711.

Josse, J. and, Eigner J., "Physical Properties of deoxyribonucleic acid," *Annu Rev Biochem*, 1966, pp. 789-834, vol. 35.

Marguet, E. and Forterre, P., "DNA stability at temperatures typical for hyperthermophiles," *Nucleic Acids Research*, 1994, pp. 1681-1686, vol. 22:(9).

Marguet, E. and Forterre P. "Protection of DNA by salts agains thermodegradation at temperatures typical for hyperthermophiles." *Extremophiles*. May 1998, pp. 115-122, vol. 2:(2).

(Continued)

*Primary Examiner*—Suryaprabha Chunduru
(74) *Attorney, Agent, or Firm*—Edwards Angell Palmer & Dodge LLP; David G. Conlin; Kathryn A. Piffat, Esq.

(57) ABSTRACT

A solution for treating a nucleic acid duplex having a pH of from 3 to 11, comprising a soluble protein or mixture of proteins; and 0.1 mM to 10 mM divalent cations; wherein the nature and concentration of the protein or mixture of proteins is selected so that the solution is capable of inhibiting heat denaturation of a nucleic acid product.

18 Claims, 4 Drawing Sheets

OTHER PUBLICATIONS

Medveczky, P., et al., "Rapid Vacuum Driven Transfer of DNA and RNA from Gels to Solid Supports," *Biotechniques*, 1987, pp. 242-246, vol. 5:(3).

Nakano, S., et al., "Nucleic acid duplex stability: influence of base composition on cation effects," *Nucleic Acids Research*, 1999, pp. 2957-2965, vol. 27:(14).

Piškur, J. and Rupprecht, A., "Aggregated DNA in ethanol solution," *FEBS Letters*, 1995, pp. 174-178, vol. 375.

Polski JM et al., Rapid and effective processing of blood specimens for diagnostic PCR using filter paper and chelex-100. *J Clin Pathol.*, 1998, pp. 215-217, vol. 51.

Reed, K.C. and Mann, D.A., "Rapid transfer of DNA from agarose gels to nylon membranes," *Nucleic Acids Research 13*: 1985, pp. 7207-7221.

Schreier, P.H., Reiss, B., Kuntz, M., "Subcellular targeting of proteins in vivo and in vitro". *Plant Molecular Biology Manual B5*. 1988, pp. 1-22.

Southern, E.M., "Detection of Specific Sequences Among DNA Fragments Separated by Gel Electrophoresis," *J. Mol. Biol.* 1975, pp. 503-517, vol. 98.

Stein D.B., and Searcy D.G., "Physiologically important stabilization of DNA by a prokaryotic histone-like protein". *Science*. 1978, pp. 219-221, vol. 202 (4364).

Towbin, H., et al., "Electrophoretic transfer of proteins from polyacrylamide gels to nitrocellulose sheets: Procedure and some applications," *Proc. Natl. Acad. Sci. USA*, 1979, pp. 4350-4354, vol. 76.

White, B.A. and Bancroft, F.C., "Cytoplasmic Dot Hybridization," *J. Biol. Chem.*, 1982, pp. 8569-8572, vol. 257:(15).

Cooper, Geoffrey M., *The Cell: A Molecular Approach*, 1997, Sinauer Associates, pp. 42-54; 316-320.

Schreier, P.H., Reiss, B., Kuntz, M., "Subcellular targeting of proteins in vivo and in vitro". Plant Molecular Biology Manual B5. (1988) 1-22.

Guagliardi A, Napoli A, Rossi M, Ciaramella M. "Annealing of complementary DNA strands above the melting point of the duplex promoted by an archaeal protein". J Mol Biol. Apr. 11, 1997;267(4):841-8.

Marguet E, Forterre P. "Protection of DNA by salts against thermodegradation at temperatures typical for hyperthermophiles." Extremophiles. May 1998; 2(2):115-22.

Stein DB, Searcy DG. "Physiologically important stabilization of DNA by a prokaryotic histone-like protein". Science. Oct. 13, 1978; 202 (4364):219-21.

* cited by examiner

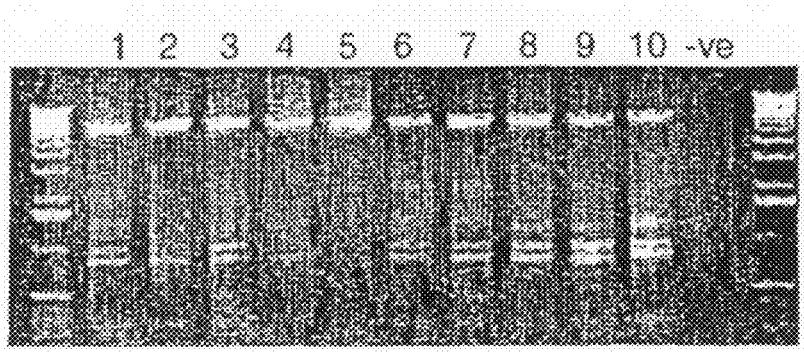
FIGURE 7A
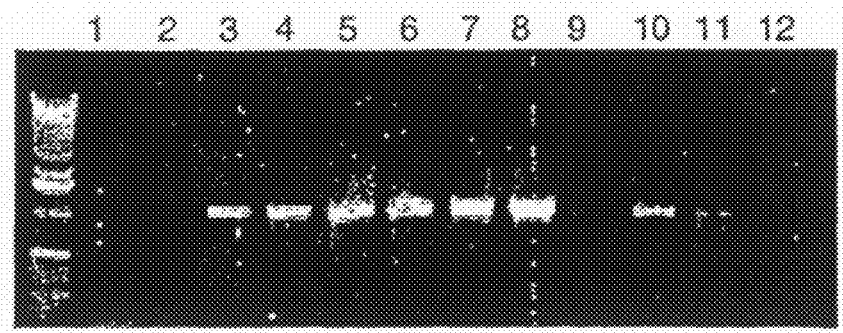
FIGURE 7B
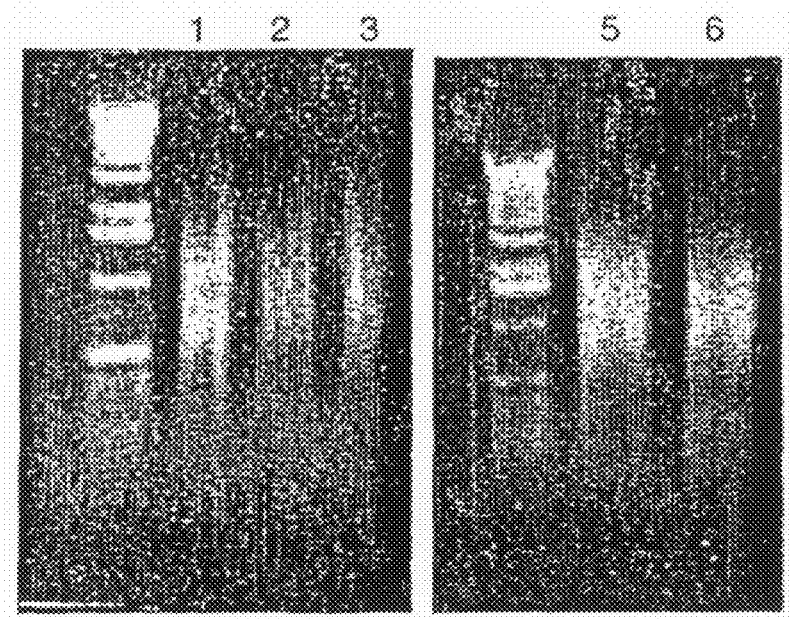
FIGURE 8A  FIGURE 8B

INHIBITING DENATURATION OF NUCLEIC ACID DUPLEXES

The present application is a divisional application of U.S. Ser. No. 10/276,886, filed Nov. 19, 2002 now U.S. Pat. No. 7,244,561, which is a 35 U.S.C. §371 national stage of PCT application PCT/GB01/02564, filed Jun. 11, 2001, which claims priority of United Kingdom Application Serial Number 0014324.8, filed Jun. 12, 2000, the disclosures of all of which are incorporated herein by reference.

TECHNICAL FIELD

This invention is in the field of nucleic acid preparation and relates to a solution for treating a nucleic acid duplex, its preparation and its uses.

BACKGROUND ART

It is well known in this art that a nucleic acid duplex which comprises two single nucleic acid strands specifically or non-specifically bound together may be separated when subjected to harsh processing conditions such as heating to an elevated temperature.

Specifically, certain DNA purification techniques require or usefully may include a heating step. It is known that in such techniques it is difficult to purify double stranded DNA, for example, from blood or other biological samples because heating causes denaturing of the double stranded DNA to form single stranded DNA. This creates a problem because many downstream DNA processing techniques, such as Southern blotting, may only be carried out usefully using a certain quantity of double stranded DNA. Accordingly, it is often necessary with some existing DNA purification techniques to return to an individual patient in order to collect further samples so that a sufficient quantity of double stranded DNA is recovered in order to be able to perform downstream analysis of the DNA.

Various forces affecting the conformation of DNA and, in particular, the stability of the double-helix structure are known. These are discussed in general terms in reference 1. Electrostatic forces attributable to ionisation, base-stacking forces, hydrogen bonding and hydrophobic forces are mentioned.

The effect of salts of 1:1 electrolytes on the thermal denaturation temperature of DNA secondary structure at neutral pH is discussed in reference 2. A lowering of the thermal denaturation temperature is observed. This effect is attributed mainly to the presence of the anions: $CCl_3COO^-$, $CF_3COO^-$, $CNS^-$ and $ClO_4^-$.

The formation of heat labile interstrand crosslinks formed when cyanomorpholinoadriamycin is reacted with DNA is the subject of reference 3. Interstrand crosslinking was detected as a resistance of DNA to separate under normal DNA denaturing conditions. The interstrand crosslinks had a midpoint melting temperature of 70° C. Clearly, these crosslinks do not inhibit heat denaturation of DNA.

A distinction is drawn in reference 4 between the problems of thermodegradation and thermodenaturation of covalently closed DNA in hyperthermic conditions. A reduction in thermodenaturation due to stabilising of the DNA primary structure in the presence of $K^+$ or $Mg^{2+}$ is reported.

A study of the effect of physiological concentrations of KCl (50-500 mM) and $MgCl_2$ (1-25 mM) on the chemical stability of double-stranded and single-stranded DNA at temperatures typical for hyperthermophiles is reported in reference 5. It is proposed that these two salts act to protect both double-stranded and single-stranded DNA against heat induced cleavage by inhibiting depurination. This effect is rationalised for double-stranded DNA by the proposal that these salts stabilise the double helix.

The effects of cation counter ion on nucleic acid duplex stability are the subject of reference 6. It is suggested that nucleic acid stability may be accounted for by nearest-neighbour interactions. A passive effect of cations bound to a double helix on nucleic acid duplex stability is suggested. It is suggested that there are preferential base pairs or nearest-neighbour base pairs for the counter ion bonding. Various physiological salt concentrations were studied.

A physiological stabilisation of DNA by a prokaryotic histone-like protein is reported in reference 7. It is stated that DNA associated with a protein which closely resembles the histones of eukaryotes is more stable than free DNA against thermal denaturation by about 40° C. The protein is tightly bound to the DNA.

Reference 8 reviews the factors that might contribute to the stability of the genomes of hypothermophiles. Extrinsic factors such as the intracellular ionic environment and so-called histone-like DNA binding proteins are discussed. It is mentioned that circular DNA molecules are intrinsically more resistant to heat denaturation than are linear DNA molecules. The role of DNA binding proteins in eukaryotes and prokaryotes in genome compaction and thermostabilisation is suggested.

A specific histone from a family of archaeal histones that bind and compact DNA molecules into nucleosome-like structures is the subject of reference 9. It is stated that the DNA-binding and compacting activities of the protein are resistant to heat inactivation, for example at 95° C. for 5 minutes. This feature is suggested as a mechanism to resist heat denaturation of DNA.

Reference 10 relates to protecting DNA from thermal denaturation using the non-specific binding protein Sso7d of the hyperthermophilic archaeon *Sulfolobus solfataricus*. The authors report on promotion of renaturation of complementary DNA strands at temperatures above the melting point of the duplex by the non-specific DNA-binding protein.

In reference 11 the effect of ethanol concentration on the thermal stability and structure of aggregated DNA in an ethanol-water solution is discussed. It is observed that with increasing ethanol concentration the melting point of DNA decreases. It is stated that at a critical ethanol concentration aggregation of the DNA molecules sets in and that aggregated DNA molecules are thermally more stable than dissolved ones. The effect of the nature of the counter ion on the stability of aggregated DNA is considered to some extent.

In view of the above, there still remains a problem to provide a simple, cost-effective method of inhibiting denaturation such as heat denaturation of a nucleic acid duplex or, more specifically, a double-stranded DNA.

Accordingly, the present invention aims to at least partially address the above problem.

DISCLOSURE OF THE INVENTION

The invention provides a solution for treating a nucleic acid duplex which is capable of inhibiting denaturation such as heat denaturation of a nucleic acid duplex or, more specifically, a double-stranded DNA.

The invention provides a solution for treating a nucleic acid duplex having a pH of from 3 to 11, comprising: a soluble protein or mixture of proteins; and 0.1 mM to 10 mM divalent cations, wherein the nature and concentration of the protein or mixture of proteins is selected so that the solution is capable of inhibiting heat denaturation of a nucleic acid duplex.

Once a nucleic acid duplex has been contacted with the solution of the invention, this enables the nucleic acid duplex to undergo more stringent processing conditions without extensive denaturation of the duplex.

In a further aspect, the invention provides use of the solution of the invention for inhibiting heat denaturation of a nucleic acid complex.

The invention also provides a method for making a solution, comprising the steps of:
(i) preparing a solution containing 0.1 mM to 10 mM divalent cations and optionally 0.1 mM to 10 mM monovalent cations;
(ii) introducing a protein or mixture of proteins to the solution prepared in step (i);
(iii) optionally adjusting the pH;

wherein the pH is in the range 3 to 10 and the nature and concentration of the protein or mixture of proteins is selected so that the solution is capable of inhibiting heat denaturation of a nucleic acid duplex.

The invention also provides a method for inhibiting heat denaturation of a nucleic acid duplex comprising the step of contacting the solution of the invention with a nucleic acid duplex.

Methods of purifying a nucleic acid duplex and Northern or Southern blotting including the step of contacting the solution of the invention with a nucleic acid duplex are also provided.

There is further provided a kit for isolating nucleic acid from a sample comprising cells containing nucleic acid comprising:
(a) a filter supported by a support;
(b) a solution according to the invention.

Specifically, according to the invention, the nucleic acid duplex may be a DNA-DNA, RNA-DNA or RNA-RNA duplex.

The effectiveness of the solution of the invention is dependent on pH. Therefore, the solution should have a pH of from about 3 to about 11. The pH may be controlled using any physiological or biological buffer, such as Tris, PIPES or HEPES.

A solution having a pH in the range of about 3 to about 11 is in accordance with the invention. Under more acidic conditions DNA undergoes depurination and structural degradation. At a more alkaline pH double-stranded DNA tends to denature to form single-stranded DNA. Particularly in the context of inhibiting denaturation of double-stranded DNA, it has been found that a solution of the invention having a pH in the range of from 8 to 9 is optimal.

The presence of a soluble protein or mixture of proteins is very important to the functioning of the solution. It is envisaged that the nature of the protein or mixture of proteins may take any form and any concentration may be used so long as the solution is capable of inhibiting heat denaturation of a nucleic acid duplex. This functional requirement may be readily tested by the skilled person by a comparison of resistance to heat denaturation of a nucleic acid duplex sample or, more specifically, a double-stranded DNA sample resuspended in (i) the solution of the invention and (ii) a standard wash solution, namely water or a low salt nucleic acid preserving solution such as AE or the like. For the purposes of the invention, a solution may be taken to be capable of inhibiting heat denaturation of a nucleic acid duplex if resistance to heat denaturation in the circumstances described above is observed to any extent.

It is envisaged that the source of the soluble protein or mixture of proteins may range from milk to a mammalian blood serum component or mixture of components or the like. Mammalian blood serum may be obtained by any process involving the separation of the cellular component of mammalian blood from a non-cellular fraction. Examples of techniques currently employed in this process include separation by filtration or by centrifugation.

Components within a blood serum can be isolated using a variety of techniques. An affinity capture technique using columns modified with DNA can be used to capture any active components as they pass through the column. Details of such a technique can be found in reference 12. Also, a fractionation technique involving fractionation of a protein solution by ultra-centrifugation using salt gradients can be used. Details of such a technique can be found in reference 13. These techniques allow the identification of an active fraction of a blood serum. The active fraction can then be analysed further to determine the exact nature of the protein(s) involved.

Another methodology for isolating the components of a blood serum would involve:
(i) performing SDS-PAGE on the blood serum;
(ii) preparing a solution of the invention containing the blood serum;
(iii) using the prepared solution in the DNA extraction process of the invention as described below;
(iv) performing SDS-PAGE on the eluate of the solution of the invention;
(v) re-using the eluate in a further DNA extraction process of the invention;
(vi) performing SDS-PAGE on the new eluate of the solution of the invention;
(vii) repeating steps (v) and (vi) as required; and
(viii) comparing the SDS-PAGE results.

Components of interest in the blood serum can be identified by depletion studies of the SDS-PAGE results. Depletion indicates binding of a component to DNA held on the filter. Repeating steps (v) and (vi) eventually leads to the loss of a particular band or bands observed by SDS-PAGE. Subsequent protein transfer by Western blotting [14] followed by standard N-terminal sequencing techniques would allow the protein(s) of interest to be identified.

The invention also provides a solution for treating a nucleic acid duplex having a pH of from 3 to 11, comprising a mammalian blood serum or mammalian blood serum component; and 0.1 mM to 10 mM divalent cations wherein the nature and concentration of the mammalian blood serum or mammalian blood serum component is selected so that the solution is capable of inhibiting heat denaturation of a nucleic acid duplex.

A fetal calf whole blood serum or adult bovine whole blood serum comprising a mixture of proteins has been found to be particularly effective in inhibiting heat denaturation of a nucleic acid duplex when included in the solution of the invention. A preferred concentration for the fetal calf blood serum or adult bovine blood serum is about 0.1% to about 5.0%, more preferably about 1.2%.

It is envisaged that the skilled person will be able to select by routine methods of experimentation a candidate soluble protein or mixture of proteins for use in the present solution and to optimise its concentration. For example, a candidate may be selected using standard protein purification procedures for example, fractionation or specific capture.

It has been found that it is preferable for the protein or mixture of protein to be treated by a modification process to improve the capability of the solution to inhibit heat denaturation of a nucleic acid duplex. Without wishing to be bound by theory, it is thought that the modification process must cause the protein to undergo a conformational change and possibly also must denature the protein.

The modification process itself or the extent of modification is not important so long as the resultant protein or mixture of proteins incorporated into the solution of the invention is modified so that the protein or mixture of proteins still is soluble and the capability of the solution to inhibit heat denaturation of a nucleic acid duplex is improved. Modification of the protein or mixture of proteins may be effected chemically or physically. When modified by heating, the skilled person would be able to optimise the processing conditions by varying the temperature and time of heating in a heat modification step.

For the purposes of the present invention, the protein or mixture of proteins will be "modified" after treating by a heating process as described above.

It is preferred that when fetal calf blood serum or adult bovine serum is used in the present solution it is modified by heating at a temperature of from 30° C. to 76° C. Preferably, it is modified by heating at about 56° C. for 30 minutes.

It should be noted here that the effectiveness of the solution of the invention is not batch sensitive. In other words, results obtained using one batch of a particular protein serum are substantially the same as results obtained under otherwise identical conditions using a second batch of the same type of protein serum.

Without wishing to be bound by theory, it is thought that the protein in the solution causes a stability change in the nucleic acid duplex. It is thought that the stability change may involve the protein loosely wrapping-around or even coiling around the duplex as a result of specific or non-specific binding to the protein. An analogy could be drawn with the action of a histone condensing DNA into chromosomes. Alternatively, it is thought that the stability change may involve the duplex loosely wrapping around or coiling around the protein.

The effectiveness of the solution has been found to be dependent upon the presence of divalent cations at a concentration of from about 0.1 mM to about 10 mM. Within this range, the action of the solution to inhibit denaturation of has been found to be optimal. The presence of divalent cations at a concentration outside this range has been found to render the solution not capable of effectively inhibiting denaturation of a nucleic acid.

A preferred concentration for the divalent cations is about 3 mM. Preferred divalent cations are $Mg^{2+}$ ions.

It is preferred that a solution of the invention additionally contains about 0.1 mM to about 10 mM monovalent cations, although the presence of monovalent cations in the solution is not essential. Within this range, the action of the present solution to inhibit denaturation of has been found to be optimal. The presence of monovalent cations at a concentration outside this range in the solution has been found to render the solution not capable of effectively inhibiting denaturation of a nucleic acid duplex.

A preferred concentration for the monovalent cations is about 8 mM. Preferred cations are $K^+$ or $Na^+$ ions.

One preferred solution of the invention comprises 3 mM $MgCl_2$, 8 mM KCl, 10 mM Tris pH 7.7 and 1.0 to 1.2% fetal calf serum.

The specific combination of the above components in the solution has unexpectedly been found effectively to inhibit heat denaturation of a nucleic acid duplex after the solution is contacted with the nucleic acid duplex. The extent of inhibition may range from a relatively small degree to substantially complete inhibition depending on the pH of the solution; the nature and concentration of the divalent cations; the nature and concentration of the soluble protein or mixture of proteins; and the potentially denaturing conditions to which the duplex is subjected, for example, the temperature and duration of heating.

It is preferable that the extent of inhibition is optimised so that in excess of 50%, preferably 70-80%, of a nucleic acid duplex sample is maintained in the duplex form when the sample is subjected to a temperature of 90° C. for up to 30 minutes, more preferably 100° C. for up to 1 hour.

A solution of the invention may be prepared by any convenient method for mixing the components in solution. However, it is preferred that a solution containing the optionally modified, soluble protein or mixture of proteins is added to the solution last. This is to ensure that the protein is not precipitated upon addition.

When the present solution contains monovalent cations, it is preferable that these are added to the solution containing the divalent cations in step (i).

Accordingly, a preferred method for making a solution of the invention comprises the steps of:
 (i) preparing a solution containing 0.1 mM to 10 mM divalent cations and optionally, 0.1 mM to 10 mM monovalent cations;
 (ii) introducing an optionally modified, protein or mixture of proteins to the solution prepared in step (i);
 (iii) optionally adjusting the pH;

wherein the pH is in the range 3 to 10 and the nature and concentration of the protein or mixture of proteins is selected so that the solution is capable of inhibiting heat denaturation of a nucleic acid duplex.

The solution may be used in any method where it is desirable to inhibit heat denaturation of a nucleic acid duplex, specifically to inhibit heat denaturation of double-stranded DNA.

One example of such a method is a method for extracting or purifying double-stranded DNA from, for example, a biological sample comprising cells, such as blood.

It has been found that yields of double-stranded DNA equivalent to yields obtained by a salting-out method are obtainable by using the present solution in the process set out in reference 15. The process involves the steps of:
 (a) applying a sample comprising cells containing nucleic acid to a filter, whereby the cells are retained as a retentate and contaminants are removed;
 (b) lysing the retentate from step (a) whilst the retentate is retained by the filter to form a cell lysate containing the nucleic acid;
 (c) filtering the cell lysate with the filter to retain the nucleic acid and remove remaining cell lysate;
 (d) washing the nucleic acid retained by the filter with the present solution; and
 (e) heating the nucleic acid to an elevated temperature whilst retained by the filter; and
 (f) eluting the nucleic acid, wherein the filter composition and dimensions are selected so that the filter is capable of retaining the cells and the nucleic acid.

Preferably, step (b) comprises lysing the retentate whilst it is entrapped within the filter.

Preferably, the filter composition and dimensions are selected so that the nucleic acid is retained by the filter in step (c) substantially in the absence of ionic interaction. More preferably the filter composition and dimensions are selected so that the nucleic acid is retained by the filter by a physical retarding of the movement of a nucleic acid down the filter.

Preferably, the filter composition and dimensions are selected so that the nucleic acid is retained by the filter in step (c) in the form of a web.

Preferably, the nucleic acid is heated to an elevated temperature of from about 4° C. to 100° C. for up to 1 hour, more preferably from 60° C. to 100° C., even more preferably about 90° C. for approximately 15 minutes whilst retained by the filter.

Approximately 80 to 100% of DNA recovered using the above process is double-stranded.

Extraction of double-stranded DNA by the above method enables a required sample of double-stranded DNA to be obtained in a significantly shorter period of time as compared with previous extraction methods.

A small amount of protein which is undetectable by spectrophotometry may be present in the eluent. This small amount does not lead to any significant problems in downstream processing of the double stranded DNA product.

Further methods where protection of a nucleic acid duplex from heat denaturation is desirable include Northern and Southern blotting methods.

DNA can be transferred onto solid membranes by capillary action as described in reference 16. During this Southern blotting process DNA migrates from a gel onto a membrane, such as nylon or nitrocellulose, by simple capillary action or by an alternative method such as electro-transfer [ref. 17] or applying a vacuum [ref. 18]. Similarly, RNA can be transferred onto a membrane in a process known as Northern blotting [19]. This transfer would employ the same transfer procedures as for Southern blotting methods.

In both of these systems, immobilised nucleic acid fragments can be detected by hybridising a suitably labelled probe to the immobilized nucleic acid to form a nucleic acid duplex. By altering the conditions of the hybridisation reaction, annealing between the probe and immobilized nucleic acid can be specific or non-specific. Variables in the conditions of hybridisation include temperature and salt concentration. Hybridisation at low temperatures results in non-specific binding. Elevating the temperature results in more specific binding. Low salt levels will encourage specific binding whereas high salt concentrations encourage non-specific interactions.

Once formed, it is desirable to protect the nucleic acid duplex against denaturation during downstream processing and particularly during any washing steps. It has been found that, by contacting the solution of the invention with the nucleic acid duplex, this can be realised.

More generally, in other hybridisation systems, a nucleic acid duplex can be protected against denaturation by contacting it with the present solution. As for Southern and Northern blotting methods, the specificity of binding of a probe to a nucleic acid can be controlled by altering salt and temperature conditions. Other hybridisation systems include in situ hybridisation, detection of mutations by observing the specificity of probe binding, and analysis of microarrays when looking at the RNA content of a tissue.

These other systems do not always require the transfer of material onto a substrate. Microarrays typically employ silicon platforms or glass slides. In the context of in situ hybridisation, probes are added to specially preserved and fixed material and the resulting analysis is performed within the material of interest.

Once the nucleic acid duplex has been contacted with the present solution in any one of the above methods, the nucleic acid duplex may be subjected to more stringent downstream conditions without affecting the structure of the nucleic acid duplex. In particular the nucleic acid duplex may be subjected to more stringent wash conditions, such as washing at an elevated temperature, without affecting the structure of the nucleic acid duplex than would otherwise have been possible.

In one aspect of the present invention, it is envisaged that the efficacy of the present solution may be controlled so as to inhibit denaturation at a particular temperature of a nucleic acid duplex having a specific strength of binding whilst allowing other nucleic acid duplexes which are bound to a lesser strength to be denatured. In other words, it is possible to achieve controlled inhibition of the denaturation of, for example, specifically rather than non-specifically bound homologues or complimentary strands of DNA.

Although it is preferred that the solution of the invention is contacted with a nucleic acid duplex prior to subjecting the duplex to stringent processing conditions, for example a heating step, it is envisaged that the nucleic acid duplex could be heated to some degree followed by contacting the present solution with the duplex and then heating more vigorously.

It is envisaged that the solution of the invention also may be used in hybridisation assays such as in situ hybridisation and microarrays, PCR assays, mutation analysis, and in the methods known under the trade names FTA/FTA elute™, Genspin™ and Genprep™.

Since the solution of the invention contains substances that may be susceptible to microbial contamination optimal conditions for storage should be employed. It is likely that the final product will contain a low concentration of an antimicrobial agent such as $Na_2S_2O_5$. However, this does not appear to inhibit extraction of DNA with the present solution. Other factors that will influence storage conditions are the longevity of fetal calf serum (FCS) at 4° C., whether the efficacy of the solution reduces upon repeated freeze thawing and how quickly the solution becomes contaminated with microbes.

BRIEF DESCRIPTION OF DRAWINGS

FIGS. 7a and 7b show the results of 7.5 kb β-globin PCR and 1.3 kb β-globin PCR respectively when performed on DNA obtained from different extraction methods. Lanes 1-5 of FIG. 7(a) show assays performed on DNA extracted by a manual salting out method. Lanes 6-10 of FIG. 7(a) show assays performed on DNA extracted by the protocol of Experiment 2. In lanes 1 and 6, the assay was performed with 0.1 ml DNA template. In lanes 2 and 7, the assay was performed on 1 ml DNA template. In lanes 3 and 8, the assay was performed on 2 ml DNA template. In lanes 4 and 9, the assay was performed on 3 ml DNA template. In lanes 5 and 10, the assay was performed on 5 ml DNA template. Lanes 1-8 of FIG. 7(b) show PCR assays performed on DNA extracted by the protocol of Experiment 2. Lanes 9-12 of FIG. 7(b) show PCR assays performed on DNA extracted by a manual salting out method. In lanes 1, 2 and 9 the assay was performed with 0.01 ml DNA template. In lanes 3, 4 and 10 the assay was performed with 0.1 ml DNA template. In lanes 5, 6 and 11 the assay was performed with 1 ml DNA template. In lanes 7, 8 and 12 the assay was performed with 5 ml DNA template.

FIGS. 8a and 8b show the results of Hinf-1 restriction digests on DNA extracted by differing methods. Lanes 1-3 in FIG. 8(a) show Hinf-1 restriction digests on DNA extracted using the 10 ml protocol of Experiment 2. The NFB reagent according to the present invention was used. Lanes 5 and 6 of FIG. 8(b) show Hinf-1 restriction digests on DNA extracted using a manual salting out method.

MODES FOR CARRYING OUT THE INVENTION

Experiment 1—Effect of Rendering DNA Resistant to Heat Denaturation

Figure 1:
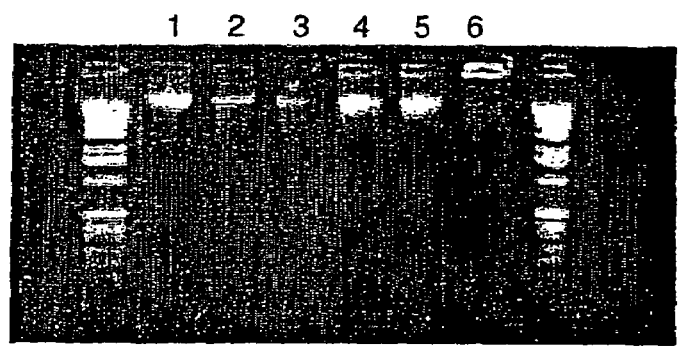
FIG. 1 shows a comparison of the resistance of double-stranded DNA to heat denaturation when suspended in the present solution as compared with resuspension in AE.

This experiment shows that DNA resuspended in the present solution (NFB reagent) is resistant to heat denaturation. Results are shown in FIG. 1. DNA was resuspended in either AE (lanes 1-3) or NFB reagent (lanes 4-6). Samples were heated at 100° C. for 1 min (lanes 1 and 4), 2.5 min (lanes 2 and 5) or 5 min (lanes 3 and 6).

Experiment 2—Genomic DNA Extraction Method Using NFB

Protocol:

|  | 1 ml | 10 ml |
|---|---|---|
| Apply blood to reaction vessel | 0.2-1 ml | 1-10 ml |
| Equal volume of RBCL | 0.2-1 ml | 1-10 ml |
| Elute to waste under vacuum |  |  |
| Apply red cell lysis buffer | 1 ml | 20 ml |
| Elute to waste under vacuum |  |  |
| Apply white cell lysis buffer | 1 ml | 20 ml |
| Elute to waste under vacuum |  |  |
| Apply wash buffer either (i) AE | 1 ml | 20 ml |
| (ii) NFB | 1 ml | 10 ml |
| Elute to waste under vacuum |  |  |
| Apply AE incubation buffer | 0.1 ml | 0.25 ml |
| Incubate at 90° C. (i) AE | 10 min | 30 min |
| (ii) NFB | 1 min | 10-20 min |
| Elute sample in AE. | 0.2 ml | 3 × 0.5 ml |

NFB reagent consists of 3 mM $MgCl_2$, 8 mM KCl, 10 mM Tris pH 7.7 and 1.2% heat modified, fetal calf serum (FCS). The efficacy of NFB to maintain double stranded DNA (dsDNA) is demonstrated using the 1 ml DNA extraction process described in the above protocol. The efficacy is diminished if the concentration of $MgCl_2$ exceeds 10 mM or falls below 0.1 mM. The action of NFB reagent is dependant on pH, with an optimal pH range observed between 8 and 9, although pH values as low as 3 and as high as 11 yield moderate amounts of dsDNA.

Replacing FCS with serum from other species (at a range of concentrations) affords partial protection from the effects of heat denaturation during the incubation stages of the DNA extraction process. This can be seen from the results in FIG. 2.

Figure 3:
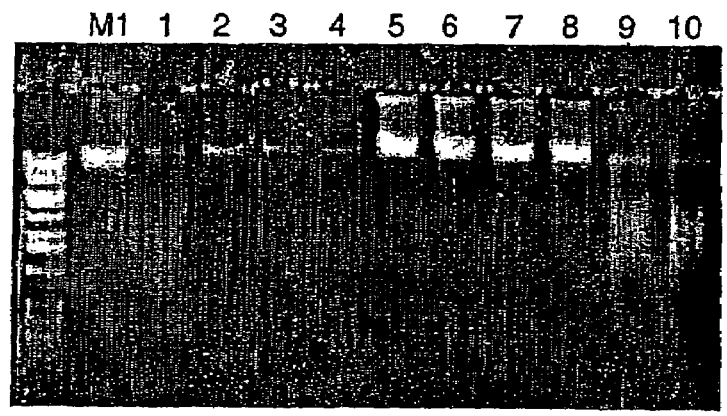
FIG. 3 shows a comparison of the yield of double-stranded DNA extracted from blood when using different extraction methods. In lanes 1 and 2, AE wash buffer was used. In lanes 3-10, a solution according to the present invention was used in place of the AE wash buffer. In lanes 3 and 4, the solution according to the present invention contained 0.1% FCS. In lanes 5 and 6, the solution according to the present invention contained 1.2% FCS. In lanes 7 and 8, the solution according to the present invention contained 2% FCS. In lanes 9 and 10, the solution according to the present invention contained 5% FCS. In all cases, the FCS was heat modified FCS. Lane M1 is a manual salting out preparation included for comparison.
Figure 5:
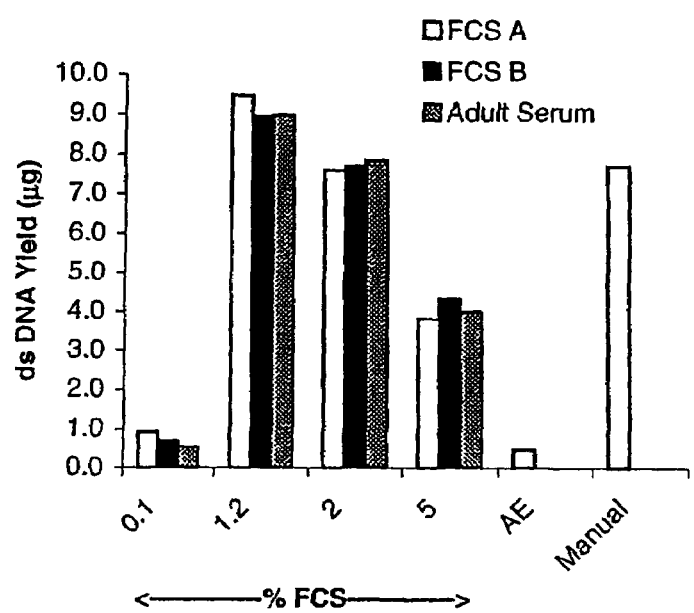
FIG. 5 shows the double-stranded DNA yield from a 1 ml blood sample when using the present solution containing fetalcalf blood serum or an adult bovine serum from different batches. Results are shown for varying concentrations of heat modified protein.

The ability of NFB reagent to prevent heat denaturation of DNA is entirely dependant on the concentration of serum used, with low (<0.1%) and high (>2%) concentrations giving lower yields of dsDNA (FIGS. 3 and 5).

It is preferred for extracting high yields of dsDNA using NFB reagent to modify the protein serum at 56° C. for 30 minutes. The effects of this can be seen from FIG. 4.

Figure 2:
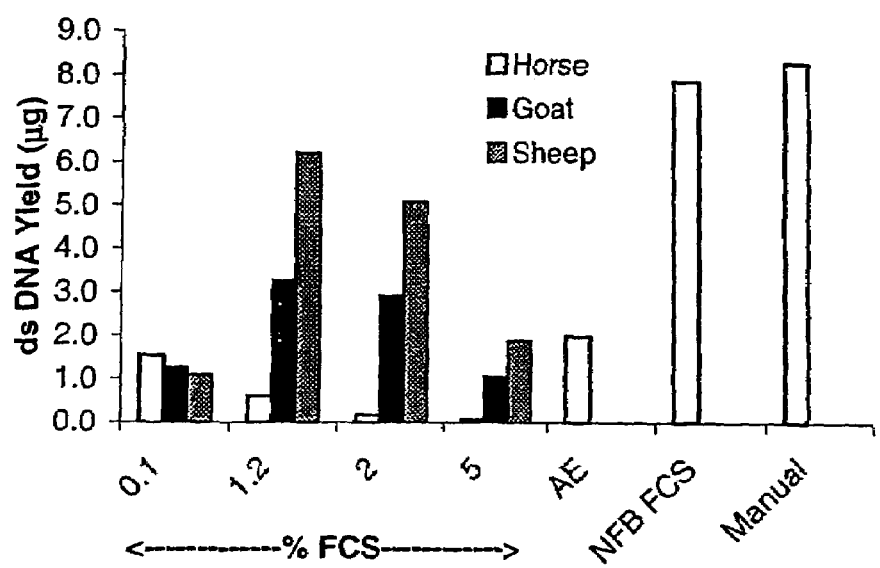
FIG. 2 shows a comparison of the yield of double-stranded DNA obtained from a sample of blood using the DNA purification process described in reference 15, when using different sources of a soluble protein or mixture of proteins.

Experiment 3—The Effect of Protein Serum Origin on Efficacy in Protecting dsDNA from Heat The effects of the present solution containing serum from various species on the yield of dsDNA recovered from 0.5 ml blood using the 1 ml DNA extraction protocol of Experiment 2 was investigated. The yields of dsDNA recovered using the same protocol in each case were compared to the yield using the present NFB reagent containing 1.2% FCS. Results from the same protocol using AE as a wash buffer and manual salting out preparations were also included for comparison. Double stranded DNA was assayed using Picogreen. Results are shown in FIG. 2.

Experiment 4—Batch Sensitivity and the Effect of Protein Concentration

This experiment shows that the concentration of protein (FCS) in the present solution is critical to the recovery of large amounts of DNA using the 1 ml extraction protocol of Experiment 2. Results are shown in FIGS. 3, 4 and 5.

AE wash buffer (lanes 1-2) was compared to the present solution containing 0.1% (lanes 3-4), 1.2% (lanes 5-6), 2% (lanes 7-8) and 5% (lanes 9-10) heat-modified FCS. Results are shown in FIG. 3.

AE wash buffer (lanes 11-12) was compared to the present solution with 1.2% unmodified FCS (lanes 13-14). Results are shown in FIG. 4.

Figure 4:
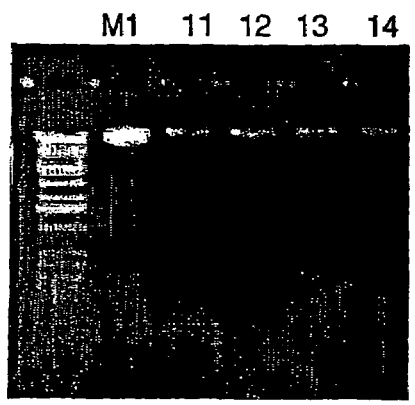
FIG. 4 shows a comparison of double-stranded DNA yield from blood when using different extraction methods. In lanes 11 and 12, AE was buffer was used. In lanes 13 and 14, a solution according to the present invention was used in place of the AE wash buffer. The solution according to the present invention contained 1.2% non-heat modified FCS. Lane M1 is a manual salting preparation included for comparison.

In both FIGS. 3 and 4, M1 is a manual salting out preparation included on each gel for comparison.

0.5 ml blood was extracted and assayed by Picogreen for the total yield of dsDNA. Different batches of FCS were used (FCS A and FCS B) along with adult bovine serum over a range of concentrations in the present solution. AE wash buffer and manual salting out preparations were included for comparison.

TABLE 1

Comparison of dsDNA yields (μg DNA per ml of blood) from 0.5 ml blood extracted using a manual salting out method or 1 ml DNA extraction process (protocol Experiment 2) with NFB reagent.

| | Experiment Number | | | | |
|---|---|---|---|---|---|
| | 1 | 2 | 3 | 4 | 5 |
| Manual Prep | 16 | 17 | 16 | 18 | 20 |
| 1 ml DNA extraction process | 18 | 18 | 16 | 36 | 24.6 |

TABLE 2

Comparison of dsDNA yields (μg DNA per ml of blood) from 10 ml blood extracted using a manual salting out method or 10 ml DNA extraction process (protocol Experiment 2) with a syringe barrel and NFB reagent.

| | Experiment Number | | | | |
|---|---|---|---|---|---|
| | 1 | 2 | 3 | 4 | 5 |
| Manual Prep | 11.6 | 6 | 6.3 | 17 | 13 |
| 10 ml DNA extraction process | 9.75 | 4.5 | 5 | 8 | 10 |

Figure 6:
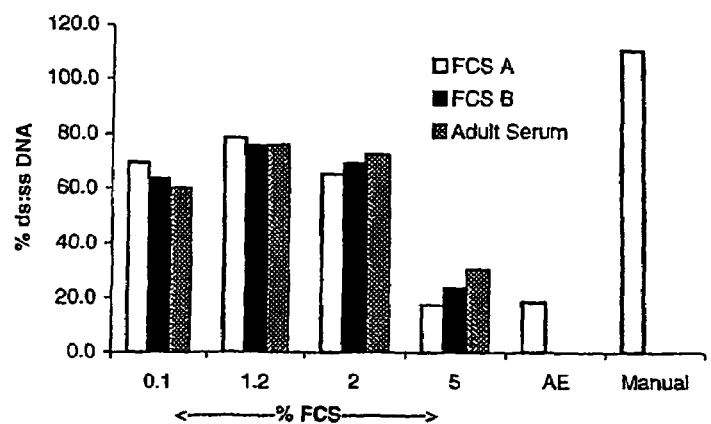
FIG. 6 shows the ratio of double-stranded to single-stranded DNA obtained from a 1 ml blood sample when using a standard AE wash buffer as compared with a solution according to the present invention. Results are shown for varying concentrations of heat modified protein.

Using NFB reagent as a wash buffer during the 1 ml DNA extraction process gives yields of both total (ss+ds) and dsDNA equivalent to that observed in manual salting out methods (FIG. 5 and Table 1). Furthermore, the amount of dsDNA recovered from blood is several fold higher using NFB reagent compared to AE wash buffer (FIG. 5). 70-80% of the total DNA recovered from blood using NFB reagent is double stranded compared to 20% with AE wash buffer (FIG. 6). It should be noted that in many instances only 80-90% of the DNA recovered using a manual salting out method is dsDNA.

Interestingly when using recycled columns consisting of 50 ml syringe barrels for a 10 ml DNA extraction process, yields of dsDNA are slightly less than that observed in a manual salting out method (Table 2). This suggests that reusing columns have some effect on DNA recovery, other data suggests that column assembly has a critical effect. Heating of the columns can cause distortions and the likely reason for lower yields with reused columns is that the heat has affected the frit/column interface.

Experiment 5—Effect of Column Type on Yield of dsDNA

The 10 ml DNA extraction protocol of Experiment 2 was repeated using the 10 ml disposable column shown in FIG. 12. The 10 ml disposable column has a unique design that allows the efficient capture of blood leukocytes. Leukocytes are entrapped in a glass fiber filter (GF/L) that is supported by a 35μ pore size, 1.5 mm thick polyethylene frit. A compression ring that is located above the GF/L allows easy assembly and prevents dislocation of the filter frit arrangement during transport. This is aided by a 0.2 mm reduced diameter located at the bottom of the column allowing an interference fit between the frit/filter and column. An upper cap attached to the column can be used to prevent or control preferential sample flow through one particular column when processing multiple samples through multiple columns. A snap off nozzle plug can be used during the incubation stages to prevent sample contamination of the heating block. Finally, a spur situated near the nozzle allows the columns to be polarized on a vacuum manifold thus preventing contact through the lids of adjacent columns. The new disposable column produces consistently higher yields of dsDNA (Table 3), equivalent to that observed in a manual salting out method. This suggests that the disposable column is assembled more precisely than the older syringe barrel column.

TABLE 3

Figure 11:
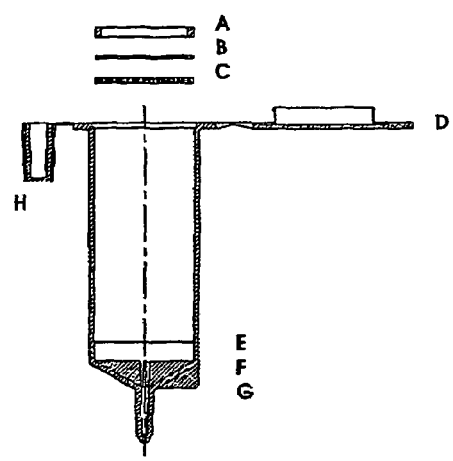
FIG. 11 is an illustration of a 10 ml disposable column. A is a compression ring; B is a GF/L filter; C is a frit; D is an upper cap; E is an area of interference fit (reduce column diameter by 0.2 mm); F is the base of column; G is a spur for polarising columns on a vacuum manifold; and H is a nozzle cap.

Comparison of dsDNA yields (μg DNA per ml of blood) from 10 ml blood extracted using a manual salting out method or 10 ml DNA extraction process (protocol Experiment 2) with the column of FIG. 11 and NFB reagent. Variation may be due to column inconsistency with 10 ml preparations.

| | Experiment Number | | | | |
|---|---|---|---|---|---|
| | 1 | 2 | 3 | 4 | 5 |
| Manual Prep | 7.4 | 7.35 | 7.5 | 7.35 | 7.4 |
| 10 ml DNA extraction process | 9.3 | 9.9 | 10.3 | 5.1 | 6 |

Experiment 6—Downstream Processing of DNA Extracted Using the Present Solution

Downstream processing of DNA extracted using the present buffer shows that both long (7.5 kb β-globin) and short (1.3 kb β-globin) range single locus PCR assays perform equally well and in some instances better compared to DNA extracted using a manual salting out method (FIGS. 7 *a* & *b*).

FIGS. 7*a* & 7*b* show β-globin single locus gene PCR assays for (a) long (7.5 kb) and (b) short (1.3 kb) range products was performed. The 7.5 kb β-globin assay was performed on Experiment 2 protocol (lanes 6-10) or manual salting out (lanes 1-5) extracted DNA with 0.1 μl (lanes 1 and 6), 1 μl (lanes 2 and 7), 2 μl (lanes 3 and 8), 3 μl (lanes 4 and 9), and 5 μl (lanes 5 and 10) DNA template. The 1.3 kb assay was performed using 0.01 μl (lanes 1, 2 and 9), 0.1 μl (lanes 3, 4 and 10), 1 μl (lanes 5, 6 and 11) and 5 μl (lanes 7, 8 and 12) template for Experiment 2 protocol (lanes 1-8) and manual salting out (lanes 9-12) extracted DNA.

Figure 9:
FIG. 9 shows the results of EcoR1 restriction digests on DNA extracted by differing methods. Lanes 1-3 of FIG. 9 show EcoR1 restriction digest on DNA extracted using the 10 ml protocol of experiment 2. Lane 4 shows an EcoR1 restriction digest on DNA using a manual salting out method.

Extracting DNA from a 10 ml sample volume yields dsDNA of sufficient concentration to perform a range of restriction enzyme digests (FIGS. 8 & 9).

FIG. 8 shows Hinf-1 restriction digests on DNA extracted using one of (a) the method according to the 10 ml Experiment 2 protocol (lanes 1-3) using NFB reagent or (b) a manual salting out method (lanes 5-6). The digests are almost identical.

FIG. 9 shows EcoR1 restriction digests on DNA extracted using one of (a) the method according to the 10 ml Experiment 2 protocol (lanes 1-3) using NFB reagent or (b) a manual salting out method (lane 4).

Figure 10A:
FIG. 10 shows the results of Mungbean nuclease digests on DNA extracted by differing methods. Lanes 1-3 of FIG. 10(a) show Mungbean nuclease digests on DNA extracted using the NFB reagent according to the present invention in the 10 ml protocol of Experiment 2. Lanes 4-6 show Mungbean nuclease digests on denatured DNA. Lanes 7-9 show undigested samples of DNA extracted using the 10 ml protocol of experiment 2. Lanes 10 and 11 show Mungbean nuclease digests on DNA extracted using a manual salting out method. Lanes 12 and 13 show Mungbean nuclease digests for denatured DNA. Lane 14 shows an undigested DNA sample extracted using a manual salting out method.
Figure 10B:
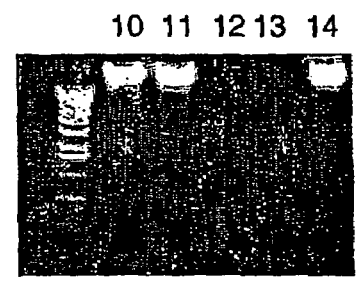

DNA extracted from blood using the NFB reagent is resistant to digestion using Mungbean nuclease, which digests specifically single stranded DNA (FIGS. 10 (a) and (b)).

FIG. 10 shows Mungbean nuclease digests on DNA extracted using one of (a) the method according to the 10 ml Experiment 2 protocol using NFB reagent (lanes 1-3) or (b) a manual salting out method (lanes 10-11). For both Experiment 2 protocol and salting out methods, denatured DNA samples were included as controls (a) lanes 4-6 and (b) 12-13, respectively. Undigested samples were also included for comparison against mungbean digested DNA in both Experiment 2 protocol (lanes 7-9) and salting out (lane 14) DNA extraction methods.

DNA extracted using the present solution has also been subjected to eight point multiplex PCR and profiles have been generated that show the DNA can be employed in such studies.

It will be understood that the invention has been described by way of example only and modifications may be made whilst remaining within the scope and spirit of the invention.

REFERENCES (THE CONTENTS OF WHICH ARE HEREBY INCORPORATED IN FULL)

1. Josse & Eigner (1966) *Annu Rev Biochem* 35:789-834.
2. *JACS* (1962) 84:1329-1338.
3. *Nucleic Acids Research* (1993) 21:1857-1862.
4. *Nucleic Acids Research* (1994) 22:1681-1686.
5. *Extremophiles* (1998) 2:115-122.
6. *Nucleic Acid Research* (1999) 27:2957-2965.
7. *Science* (1978) 202:219-221.
8. *Advances in Protein Chemistry* (1996) 48:437-467.
9. *FEMS Microbiology Reviews* (1996) 18:203-213.
10. *J. Mol. Biol.* (1997) 267:841-848.
11. *FEBS Letters* (1995) 375:174-178.
12. *Biochem. Biophys Acta.* (1975) 378: 424-438.
13. *J. Dairy Sci.* (1972) 55:696-711.
14. *Proc. Natl. Acad. Sci. USA.* (1979) 79:4350-4354.
15. International patent application WO00/21973 (PCT/GB99/03357).
16. Southern (1975) *J. Mol. Biol.* 98:503-517.
17. Reed & Mann (1985) *Nucleic Acids Research* 13:7207-7221.
18. Medveczky et al (1987) *Biotechniques* 5:242ff.
19. White & Bancroft (1982) *J. Biol. Chem.* 257: 8569ff.

The invention claimed is:

1. A kit for isolating nucleic acid from a sample comprising cells containing nucleic acid, comprising: (a) a filter supported by a support; (b) a solution having a pH of from 3 to 11 and comprising (1) a soluble protein or mixture of proteins and (2) 0.1 mM to 10 mM divalent cations, wherein:
    (a) the nature and concentration of the protein or mixture of proteins is selected so that the solution is capable of inhibiting heat denaturation of a nucleic acid duplex; and
    (b) the protein or mixture of proteins comprises whole fetal calf blood serum or whole adult bovine serum.

2. A solution having a pH of from 3 to 11 and comprising (a) a soluble protein or mixture of proteins and (b) 0.1 mM to 10 mM divalent cations, wherein:
    (a) the nature and concentration of the protein or mixture of proteins is selected so that the solution is capable of inhibiting heat denaturation of a nucleic acid duplex, for inhibiting heat denaturation of a nucleic acid duplex and extracting double-stranded DNA from a biological sample comprising cells; and
    (b) the protein or mixture of proteins comprises whole fetal calf blood serum or whole adult bovine serum.

3. The kit of claim 1, wherein the protein or mixture of proteins in the solution is treated by a modification process to improve the capability of the solution to inhibit heat denaturation of a nucleic acid duplex.

4. The kit of claim 1, wherein the solution further comprises 0.1 mM to 10 mM monovalent cations.

5. The kit of claim 1, wherein the protein or mixture of proteins in the solution comprises a mammalian blood serum component.

6. The kit of claim 1, wherein the protein or mixture of proteins comprises about 0.1% to 5.0% serum.

7. The kit of claim 1, wherein the solution comprises about 3 mM divalent cations.

8. The kit of claim 7, wherein the divalent cations comprises $Mg^{2+}$ ions.

9. The kit of claim 1, wherein the solution comprises about 8 mM monovalent cations.

10. The kit of claim 9, wherein the monovalent cations comprise $K^+$ or $Na^+$ ions.

11. The kit of claim 1, wherein the solution has a pH of from 8 to 9.

12. The kit of claim 1, wherein the solution further comprises a physiological buffer.

13. The kit of claim 12, wherein the physiological buffer is Tris.

14. The kit of claim 1, wherein the solution comprises 3 mM $MgCl_2$, 8 mM KCl, 10 mM Tris pH 7.7 and 1.2% fetal calf serum.

15. The kit of claim 1, further comprising one or more solutions selected from the group consisting of a red cell lysis solution, a solution for rupturing intact whole cells to leave condensed nuclear material, a lysis solution for lysing nuclear material and an elution solution.

16. The kit as defined in any one of claims 1, 3-5, and 6-15, used in a method for isolating nucleic acid from a sample comprising cells containing nucleic acid.

17. The solution of claim 2, wherein the solution is as defined in any one of claims 3-5 and 6-14.

18. The solution of claim 2 or claim 17, used in a method of Northern or Southern blotting.

* * * * *